United States Patent
Sweeney et al.

(10) Patent No.: US 7,479,112 B2
(45) Date of Patent: Jan. 20, 2009

(54) ACOUSTIC PHYSIOLOGICAL SENSOR

(75) Inventors: Robert J. Sweeney, Woodbury, MN (US); Douglas R. Daum, Oakdale, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 489 days.

(21) Appl. No.: 10/648,837

(22) Filed: Aug. 26, 2003

(65) Prior Publication Data

US 2005/0049492 A1  Mar. 3, 2005

(51) Int. Cl.
A61B 5/02 (2006.01)
(52) U.S. Cl. .................. 600/528; 600/508
(58) Field of Classification Search ............. 600/411, 600/437, 528
See application file for complete search history.

(56) References Cited

U.S. PATENT DOCUMENTS

| | | | | |
|---|---|---|---|---|
| 4,345,588 A * | 8/1982 | Widder et al. | ................. | 600/12 |
| 4,703,756 A * | 11/1987 | Gough et al. | ................ | 600/347 |
| 4,849,210 A * | 7/1989 | Widder | .................... | 424/9.322 |
| 5,062,841 A * | 11/1991 | Siegel | ..................... | 604/891.1 |
| 5,156,154 A * | 10/1992 | Valenta et al. | ............. | 600/455 |
| 5,161,536 A * | 11/1992 | Vilkomerson et al. | ....... | 600/443 |
| 5,188,106 A * | 2/1993 | Nappholz et al. | ............ | 607/24 |
| 5,305,745 A * | 4/1994 | Zacouto | ...................... | 600/324 |
| 5,324,297 A * | 6/1994 | Hood et al. | ................... | 606/99 |
| 5,445,155 A * | 8/1995 | Sieben | ....................... | 600/443 |
| 5,843,156 A * | 12/1998 | Slepian et al. | ............. | 128/898 |
| 6,123,923 A * | 9/2000 | Unger et al. | ............... | 424/9.52 |
| 6,272,377 B1 | 8/2001 | Sweeney et al. | | |
| 6,296,630 B1 * | 10/2001 | Altman et al. | .............. | 604/508 |
| 6,315,981 B1 * | 11/2001 | Unger | ..................... | 424/9.323 |
| 6,322,515 B1 * | 11/2001 | Goor et al. | .................. | 600/485 |
| 6,328,700 B1 * | 12/2001 | Rheinhardt et al. | ......... | 600/504 |
| 6,348,186 B1 * | 2/2002 | Sutton et al. | ............... | 424/9.52 |
| 6,350,463 B1 * | 2/2002 | Herman et al. | .............. | 424/425 |
| 6,409,674 B1 * | 6/2002 | Brockway et al. | ........... | 600/486 |
| 6,416,740 B1 * | 7/2002 | Unger | ....................... | 424/9.52 |
| 6,421,565 B1 * | 7/2002 | Hemmingsson | .............. | 607/17 |
| 6,537,246 B1 * | 3/2003 | Unger et al. | .................. | 604/82 |
| 6,645,147 B1 * | 11/2003 | Jackson et al. | ............. | 600/458 |
| 6,666,811 B1 * | 12/2003 | Good | ............................ | 600/8 |
| 6,751,491 B2 * | 6/2004 | Lew et al. | .................... | 600/345 |
| 6,810,286 B2 * | 10/2004 | Donovan et al. | .............. | 607/2 |
| 6,939,530 B2 * | 9/2005 | Sutton et al. | ............... | 424/9.52 |
| 7,078,015 B2 * | 7/2006 | Unger | ....................... | 424/9.52 |
| 7,083,572 B2 * | 8/2006 | Unger et al. | ................ | 600/458 |
| 7,311,731 B2 * | 12/2007 | Lesniak et al. | ............... | 623/3.1 |
| 2002/0119441 A1 * | 8/2002 | Elias | ............................ | 435/4 |
| 2002/0176849 A1 * | 11/2002 | Slepian | ..................... | 424/93.7 |
| 2003/0100822 A1 * | 5/2003 | Lew et al. | .................. | 600/365 |

(Continued)

Primary Examiner—George Manuel
Assistant Examiner—Christopher A Flory
(74) Attorney, Agent, or Firm—Schwegman, Lundberg & Woessner, P.A.

(57) ABSTRACT

This document describes, among other things, a body having at least one acoustically detectable property that changes in response to a change in a physiological condition, such as ischemia. The body is positioned with respect to a desired tissue region. At least one acoustic transducer is used to acoustically detect a change in physical property. In one example, the body is pH sensitive and/or ion selective. A shape or dimension of the body changes in response to pH and/or ionic concentration changes resulting from a change in an ischemia state. An indication of the physiological condition is provided to a user.

46 Claims, 5 Drawing Sheets

U.S. PATENT DOCUMENTS

| | | | |
|---|---|---|---|
| 2004/0215049 A1* | 10/2004 | Zdeblick et al. | 600/16 |
| 2004/0258614 A1* | 12/2004 | Line et al. | 424/1.11 |
| 2004/0260346 A1* | 12/2004 | Overall et al. | 607/4 |
| 2005/0107870 A1* | 5/2005 | Wang et al. | 623/1.44 |
| 2005/0159789 A1* | 7/2005 | Brockway et al. | 607/32 |
| 2005/0234336 A1* | 10/2005 | Beckman et al. | 600/431 |
| 2006/0015146 A1* | 1/2006 | Girouard et al. | 607/3 |
| 2006/0015178 A1* | 1/2006 | Moaddeb et al. | 623/2.36 |
| 2006/0229594 A1* | 10/2006 | Francischelli et al. | 606/27 |
| 2006/0251582 A1* | 11/2006 | Reb | 424/9.41 |
| 2007/0010702 A1* | 1/2007 | Wang et al. | 600/8 |
| 2007/0015981 A1* | 1/2007 | Benaron et al. | 600/323 |
| 2008/0097227 A1* | 4/2008 | Zdeblick et al. | 600/486 |

* cited by examiner

ACOUSTIC PHYSIOLOGICAL SENSOR

TECHNICAL FIELD

This document relates generally to medical systems, devices, and methods, and particularly, but not by way of limitation, to an acoustic physiological sensor.

BACKGROUND

Physiological conditions of a subject can provide useful information about the subject's health status to a physician or other caregiver. For example, portions of a heart muscle that receive inadequate blood circulation may become ischemic. There is a need for improved techniques of invasively or noninvasively measuring changes in a physiological condition indicative of ischemia.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings which form a part hereof, and in which is shown by way of illustration specific embodiments in which the invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a "nonexclusive or," unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

Figure 1:
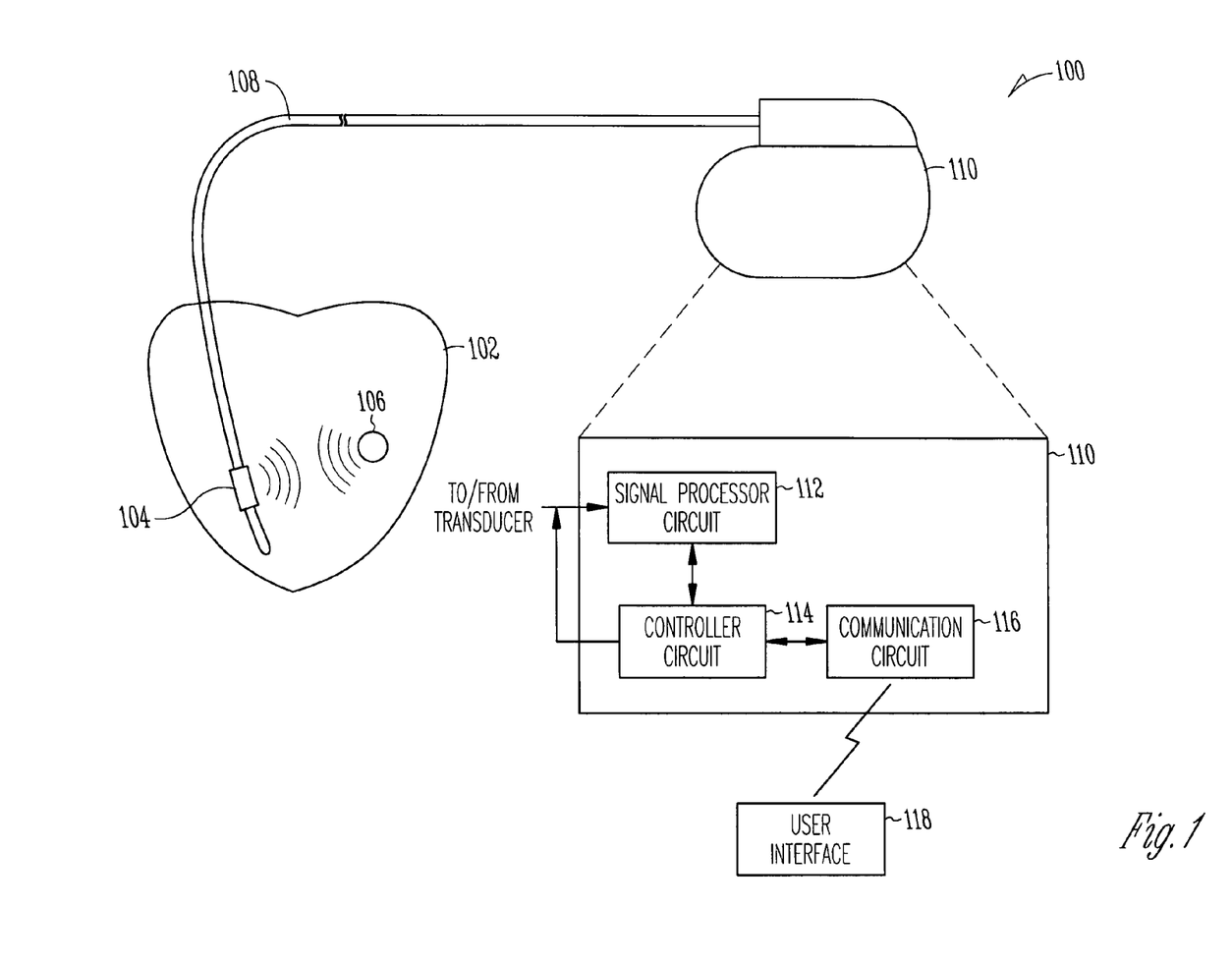
FIG. 1 is a schematic diagram illustrating generally one example of a system to detect a change in at least one physiological condition of a tissue, such as a heart.

FIG. 1 is a schematic diagram illustrating generally, by way of example, but not by way of limitation, one example of a system 100 to detect a change in at least one physiological condition of a tissue, such as tissue of a heart 102. In this example, the system includes an ultrasound or other acoustic transducer 104, which is disposed within or near the heart 102, or any other region of interest. In this example, a sphere or other body 106 is also disposed within or near the heart 102 or other region of interest, such as near the transducer 104. In this example, but not by way of limitation, the transducer 104 is located on an intracardiac lead 108, which is coupled to an implantable cardiac rhythm management (CRM) or other device 110. In one example, the spherical body 106 includes a diameter approximately between 1 micrometer and 50 micrometers, such as about 20 micrometers.

In this example, the device 110 includes a signal processor circuit 112. The signal processor circuit 112 is coupled to the transducer 104 to process an ultrasound or other acoustic signal received from the transducer 104. In this example, the device 110 also includes a controller circuit 114. The controller circuit 114 is coupled to the transducer 104 to provide at least one control signal to the transducer 104. In this example, the controller circuit 114 is also coupled to the signal processor circuit 112, such as to digitally perform additional processing on the acoustic signal. In this example, the device 110 includes a telemetry or other communication circuit 116. The communication circuit 116 is coupled to the controller circuit 114, such as to receive information about a change in at least one physiological condition of the heart 102 or other tissue or region of interest, where the change in the physiological condition is detected using an acoustic determination of a change in a physical property of the body 106. The communication circuit 116 is communicatively couplable to an external user interface 118, such as for transmitting an indication of the physical property, the change in the physical property, the physiological condition, or the change in the physiological condition for display to a user and/or recording. In one example, the external user interface 118 includes a nearby external programmer. In another example, the external user interface 118 includes an a computer network-linked (e.g., internet linked) and/or telephone network-linked more distant advanced patient management system capable of storing and/or displaying patient data and/or performing other functions. In one example, the external user interface 118 includes a short range communication circuit for communication with the implantable device 110 and an internet-linked or other long range communication circuit to communicate with an patient management computer server.

Figure 2:
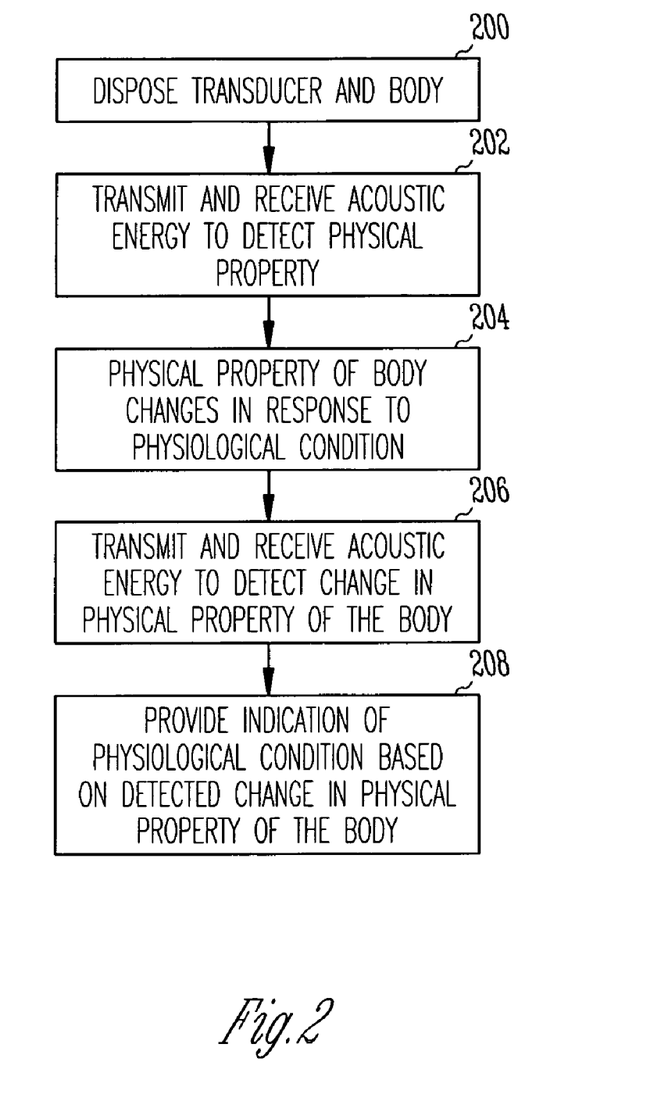
FIG. 2 is a flow chart illustrating generally a method of providing an indication of a physiological condition, such as by using the system of FIG. 1, or other desired system.

FIG. 2 is a flow chart illustrating generally, by way of example, but not by way of limitation, a method of providing an indication of a physiological condition, such as by using the system of FIG. 1 or other desired system. In the example of FIG. 2, at 200, the transducer 104 and the body 106 are disposed near the local region of tissue for which the indication of the physiological condition is desired. In one example, this includes intravascularly introducing an ultrasound transducer 104 into a right ventricular chamber of the heart 102, such as by using an intracardiac lead 108. In one example, this also includes intravascularly introducing a small spherical or other body 106 into coronary vasculature, such as via the coronary arteries or veins, to position the body 106 into contact with a local region of a microcirculatory myocardial tissue bed for which an ischemia determination is desired.

At 202, the transducer 104 transmits acoustic energy. In this example, the transmitted acoustic energy is reflected by the body 106. The reflected acoustic energy is received at the same (or different) transducer 104. The received acoustic energy is processed to obtain a first reading of a physiological condition using a physical property of the body 106.

Figure 3:
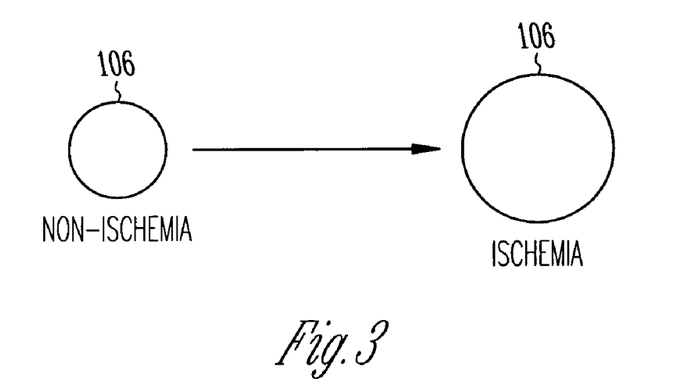
FIG. 3 is a conceptual schematic diagram illustrating generally a swelling of a spherical body from non-ischemic to ischemic conditions.

At 204, a physical property of the body 106 changes in response to a physiological condition. In one illustrative example, the size of a spherical body 106 changes in response to the physiological condition of ischemia. Ischemia results from a decreased blood flow to the heart tissue. This reduced blood flow produces several physiological effects in the extracellular portion of the ischemic tissue. For instance, the extracellular space would undergo a slight decrease in sodium (Na+) ions, a substantial increase in potassium (K+) ions, an increase in calcium (Ca++) ions, and a decreased pH due to accumulation of metabolic waste (e.g., particularly an increase in percentage carbon dioxide ($pCO_2$) and a decreased percentage oxygen ($pO_2$). In one example, the spherical or other at least one body 106 responds to the change in pH, and is constructed using a pH sensitive polymer. As a result of the decreased pH during ischemia, the body 106 adsorbs water or other bodily fluids and swells, such as illustrated in FIG. 3. This change in a physical property of the body 106 is acoustically detectable. It is believed that a 10% change in diameter of the spherical body 106 will increase the frequency of reflected acoustic energy by about 10% (e.g., from 20 MHz to 22 MHz).

At 206, the transducer 104 transmits and receives acoustic energy to obtain a second reading of a physiological condition (e.g., ischemia) using this change in a physical property (e.g., size and acoustic reflectance) of the body 106. A difference between the first and second readings permits the detection of any change in the physiological condition.

At 208, the system provides an indication of the physiological condition and/or a change in the physiological condition using any detected change in the physical property of the body 106.

FIG. 3 is a conceptual schematic diagram illustrating generally, by way of example, but not by way of limitation, a swelling of a spherical body 106 from non-ischemic to ischemic conditions, thereby increasing the frequency at which acoustic energy is reflected from the spherical body 106.

Figure 4:
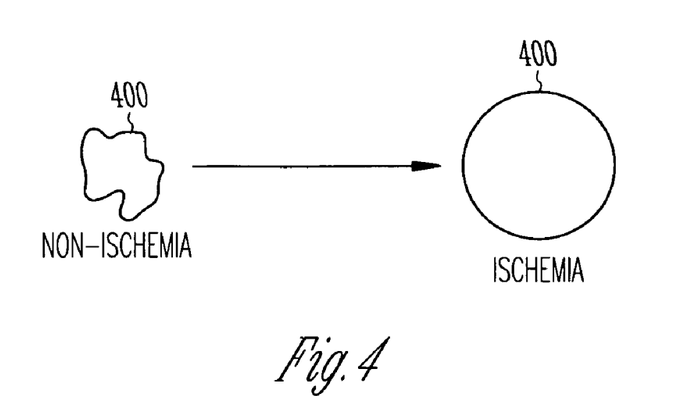
FIG. 4 is a conceptual schematic diagram illustrating generally a swelling of a body that changes its physical property of morphology, shape, or stiffness from non-ischemic to ischemic conditions.

FIG. 4 is a conceptual schematic diagram illustrating generally, by way of example, but not by way of limitation, a swelling of a body 400 (which need not be spherical). In this example, the swelling changes its physical property of morphology, shape, or stiffness from non-ischemic to ischemic conditions, thereby increasing the frequency at which acoustic energy is reflected from the body 400. In one example, the body 400 is constructed from a pH sensitive polymer or other pH sensitive material, as discussed above, to obtain the change in morphology, shape, or stiffness. In another example, the body 400 is constructed of an ion-selective membrane enclosure defining its shape. Ischemia results in an altered local concentration of sodium (Na+), potassium (K+), and calcium (Ca++). During ischemia, one or more of these variety of ions are accepted from the local environment across the membrane enclosure to within the body 400. The resulting swelling of the body 400 causes an acoustically detectable change in shape.

Figure 5:
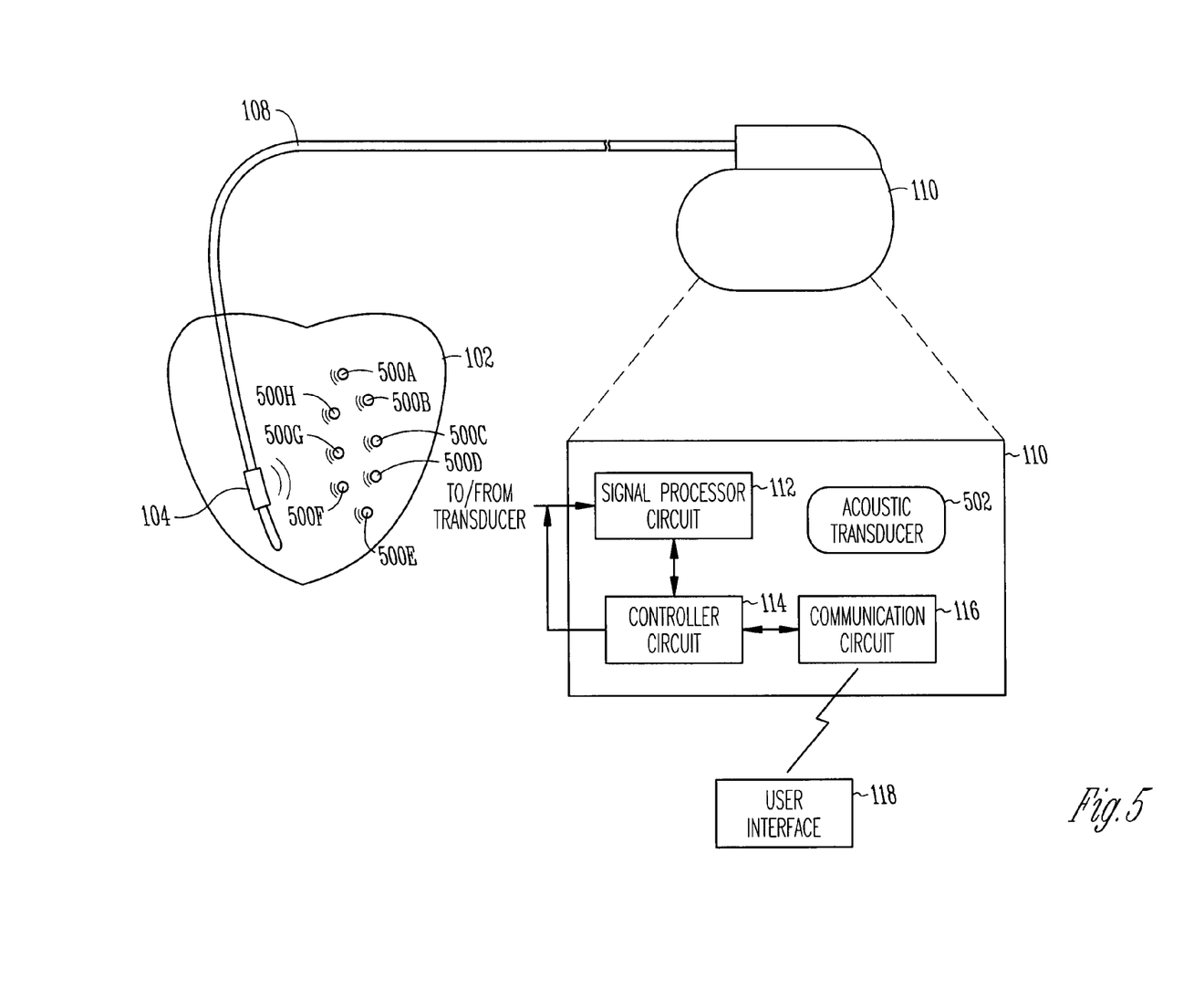
FIG. 5 is a schematic diagram, similar to FIG. 1, but illustrating a plurality of spherical or other bodies positioned at desired myocardial locations, such as described above.

FIG. 5 is a schematic diagram, similar to FIG. 1, but illustrating generally, by way of example, but not by way of limitation, a plurality of spherical or other bodies 500 positioned at desired myocardial locations, such as described above. This permits detection of a change in physiological condition over a broader region. Moreover, although the above description has generally emphasized detecting a change in physiological condition by using a change in acoustic reflectance due to a change in a physical property (e.g., size and/or shape) of the body, other techniques could rely on a change in acoustic transmission, acoustic attenuation, and/or acoustic transit time, and/or any other acoustic technique. In one example, the device 110 includes a second acoustic transducer 502 (e.g., carried within a hermetically-sealed housing enclosure of the implantable device 110, or disposed on a second intravascular catheter). In this example, acoustic energy is transmitted from the first transducer 104 and received at the second transducer 502 (or vice versa). The bodies 500 are positioned acoustically in between the transducers 104 and 502. A change in physiological condition (e.g., ischemia) alters the acoustic transmission and/or attenuation between the transducers. This is measured by the signal processor circuit 112 and the controller circuit 114.

Figure 6:
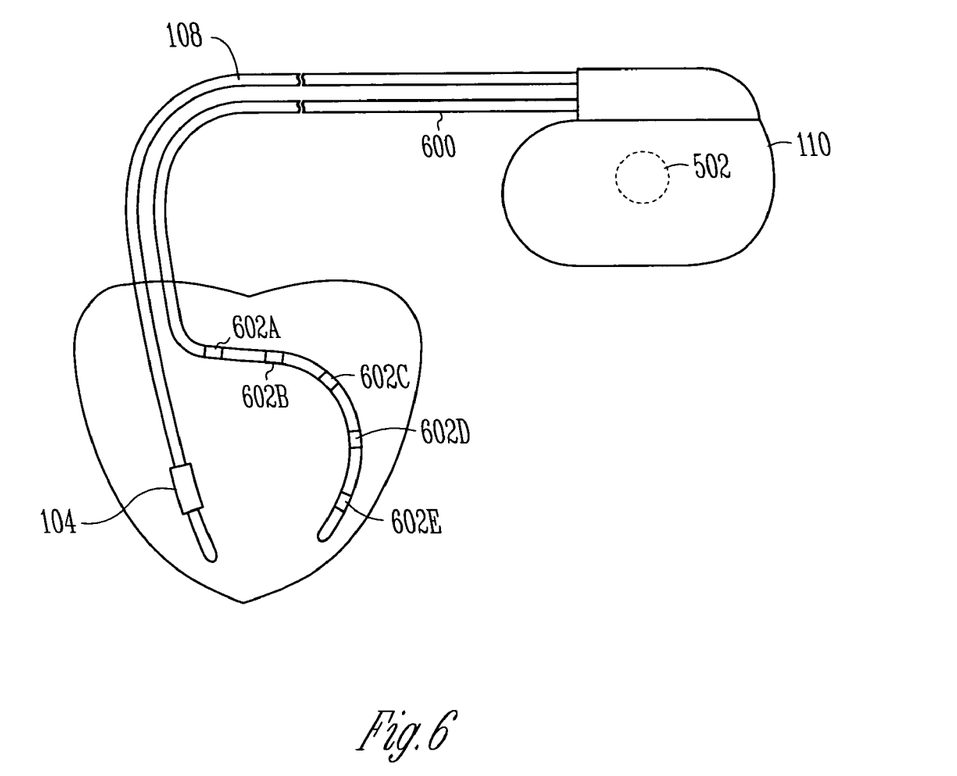
FIG. 6 is a schematic diagram, similar to FIG. 5, but illustrating an example of a second intravascular lead catheter.

FIG. 6 is a schematic diagram, similar to FIG. 5, but illustrating generally, by way of example, but not by way of limitation, a second intravascular lead catheter 600. The second intravascular lead catheter 600 includes one or more bodies 602 that swell or otherwise alter an acoustically detectable physical property in response to a change in a physiological condition, such as described above. In one example, the catheter 600 is introduced into a coronary sinus and/or great cardiac vein, such as to position the bodies 602 in contact with a myocardial tissue region of interest. Acoustic detection is performed either using the single transducer 104, as described above, or by using two transducers 104 and 502, as also described above. Alternatively, the second intravascular lead catheter provides an appropriate electrical connection to the one or more bodies 602 that swell or otherwise alter a physical property, thereby changing an electrical property (e.g., a bridge or other resistance, capacitance, etc.) incorporated within the one or more bodies 602. In this example, the ischemia or other physiological condition is detected electrically instead of acoustically.

In one example, a change in physiologic condition (e.g., ischemia) is determined from the acoustic response of the spherical or other body or bodies 602 to a change in the physiologic condition. The acoustic response is compared to a baseline acoustic response. If the acoustic response deviates from the baseline acoustic response by an amount that is greater than a predetermined threshold value, then a detected change in the physiologic condition (e.g., ischemia) is declared. In one example, the detected change in the physiologic condition is stored and/or communicated to the remote user interface 118 for storage and/or display or other presentation to the user. In one example, the detected change in the physiologic condition is used in conjunction with an alarm to alert the physician and/or the clinician (e.g., that the patient is undergoing an ischemic episode).

In another example, the detected change in the physiologic condition is used to initiate or modify therapy being delivered by the implantable cardiac rhythm management device 110. For example, if a detected ischemia episode was preceded by a time period during which pacing pulses were delivered at a relatively higher average rate, then, in one example, the pacing rate is reduced. In another example, such as where multiple pacing electrodes are disposed at different locations about the heart, the locations or sequence of delivery of pacing pulses from such locations is altered, such as to shift blood toward the ischemic area of the heart tissue. In a further example, the change in the physiologic condition is used as a factor that is predictive of the occurrence of a future episode of cardiac arrhythmia, such as fibrillation. One example of using factor(s) predictive of future arrhythmias (as well as taking preventative measures) is described in Robert J. Sweeney et al. U.S. Pat. No. 6,272,377 entitled CARDIAC RHYTHM MANAGEMENT SYSTEM WITH ARRHYTHMIA PREDICTION AND PREVENTION, which is assigned to Cardiac Pacemakers, Inc., and which is incorporated by reference herein in its entirety, including its disclosure of devices and methods for predicting and preventing future arrhythmias. In one example, the detected change in the physiologic condition is used to alter the state of the cardiac rhythm management device 110 in anticipation of a future physiologic event. For example, the device 110 could monitor the subject with greater time resolution during an ischemia episode, or could pre-charge defibrillation capacitors to more readily deliver a defibrillation pulse.

Although the above examples have emphasized use of an implantable device 110, such as for obtaining chronic measurements, alternatively, each of these examples is implemented with an external device, operating similarly.

It is to be understood that the above description is intended to be illustrative, and not restrictive. For example, aspects of the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

What is claimed is:

1. An apparatus comprising:
   an implantable transducer; and
   a physiological sensor that includes at least one biocompatible body, the body sized and shaped to be implanted into and within a myocardial wall of a subject, at least a portion of the body including a material having at least one physical property that changes in response to a physiological condition of the subject, wherein the change in the at least one physical property is responsive to at least one of a change in pH or a change in an ion concentration, wherein the portion of the body is sized and shaped such that the change in the physical property is chronically detectable using acoustic energy supplied by the implantable transducer to provide an indication of the physiological condition.

2. The apparatus of claim 1, in which the change in the physical property includes a change in size.

3. The apparatus of claim 1, in which the change in the physical property includes a change in stiffness.

4. The apparatus of claim 1, in which the change in the physical property includes a change in acoustic reflection from the body.

5. The apparatus of claim 1, in which the change in the physical property includes a change in acoustic transmission by the body.

6. The apparatus of claim 1, in which the change in the physical property includes a change in acoustic attenuation by the body 7. The apparatus of claim 1, in which the body is sized and shaped to be less than or equal to 50 micrometers in diameter.

8. The apparatus of claim 1, in which the body includes a sphere.

9. The apparatus of claim 1, in which the body comprises at least a portion of a catheter.

10. The apparatus of claim 1, further comprising an acoustic receiver to receive acoustic energy from at least one of the body and the myocardium to detect the change in the physical property of the body in response to the change in the physiological condition of the subject.

11. The apparatus of claim 10, further comprising a signal processor circuit coupled to the acoustic receiver.

12. The apparatus of claim 11, further comprising a user interface, coupled to the signal processor circuit, the user interface comprising a display that includes at least one indicator that includes information about at least one of the change in the physiological condition and the change in the physical property.

13. The apparatus of claim 12, in which the user interface includes an external programmer.

14. The apparatus of claim 12, in which the user interface includes a computer that is communicatively coupled to the signal processor circuit at least in part over a computer network or telephony network.

15. The apparatus of claim 1, in which the at least one biocompatible body is pH sensitive.

16. The apparatus of claim 1, in which the at least one biocompatible body is ion selective.

17. The apparatus of claim 1, in which the material includes at least one electrical property that changes in response to a physiological condition.

18. The apparatus of claim 1, in which the body is sized and shaped to be introduced within a vein or artery of a subject.

19. The system of claim 1, wherein the physical property changes in response to a physiological condition that is predictive of a tachyarrhythmia.

20. A system comprising:
   a plurality of biocompatible spheres, each sphere sized and shaped to be introduced into and within a myocardial wall of a subject, each sphere including at least one physical property that changes in response to a physiological condition of the subject, the at least one physical property being responsive to at least one of a change in pH or a change in an ion concentration;
   an implantable acoustic transmitter, to provide energy to the spheres and the myocardium; and
   an acoustic receiver, to receive energy from at least one of the spheres and the myocardium, wherein the change in the at least one physical property is chronically detectable using the energy to provide an indication of the physiological condition.

21. The system of claim 20, comprising an implantable medical device including a state that is altered using a change in the physical property.

22. The apparatus of claim 20, further comprising a controller circuit coupled to the acoustic receiver.

23. The apparatus of claim 22, further comprising an external interface, coupled to the controller circuit, the external interface configured to receive information based on the change in the physical property.

24. A method comprising:
   introducing a physiological sensor into and within a myocardial wall of a subject, the physiological sensor includes at least one body having at least one physical property that changes in response to at least one of a change in pH or a change in an ion concentration;

transmitting acoustic energy to the body and the myocardium, the acoustic energy transmitted using an implantable transducer;

receiving transmitted acoustic energy for detecting the change in the physical property of the body; and detecting and providing an indication of the physiological change by chronically detecting the change in the physical property of the body.

25. The method of claim 24, in which the introducing the at least one body includes introducing at least one pH sensitive body.

26. The method of claim 24, in which the introducing at least one body includes introducing at least one ion sensitive body.

27. The method of claim 24, in which the physical property that changes is a size of the body.

28. The method of claim 24, in which the physical property that changes is a stiffness of the body.

29. The method of claim 24, in which the physical property that changes is an acoustic reflection of the body.

30. The method of claim 24, in which the physical property that changes is an acoustic transmission of the body.

31. The method of claim 24, in which the physical property that changes is an acoustic attenuation of the body.

32. The method of claim 24, in which the detecting the change in the physical property of the body comprises detecting an acoustic reflection of the body.

33. The method of claim 24, in which the detecting the change in the physical property of the body comprises detecting an acoustic transmission of the body.

34. The method of claim 24, in which the detecting the change in the physical property of the body comprises detecting an acoustic attenuation of the body.

35. The method of claim 24, in which the introducing the at least one body includes introducing at least one sphere.

36. The method of claim 24, in which the introducing the at least one body includes introducing a catheter.

37. The method of claim 24, in which the introducing the at least one body includes introducing at least one body sized and shaped to be less than or equal to 50 micrometers in diameter.

38. The method of claim 24, in which the detecting the physiological change using the detected change in the physical property of the body comprises detecting ischemia using the detected change in the physical property of the body.

39. The method of claim 24, in which the detecting the physiological change using the chronically detected change in the physical property of the body comprises detecting blood flow using the chronically detected change in the physical property of the body.

40. The method of claim 24, further comprising introducing a catheter for at least one of the transmitting the acoustic energy and the receiving the acoustic energy.

41. A system comprising:

a physiological sensor that includes one or more biocompatible bodies, the one or more bodies sized and shaped to be implanted into and within a myocardial wall of a subject, at least a portion of the one or more bodies including a material having at least one physical property that changes in response to a physiological condition of the subject, wherein the change in the at least one physical property is responsive to at least one of a change in pH or a change in an ion concentration, and wherein the at least a portion of the one or more bodies is sized and shaped such that the change in the physical property is chronically detectable using acoustic energy to provide an indication of the physiological condition; and an implantable medical device, including one or more acoustic transducers configured to provide acoustic energy to the one or more bodies and to receive responsive acoustic energy, the implantable medical device configured to detect and provide an indication of a change in the physiological condition by using the responsive acoustic energy to detect the change in the physical property of the one or more bodies.

42. The system of claim 41, wherein the implantable medical device includes an intravascular lead that includes one or more acoustic transducers.

43. The system of claim 41, comprising:

a first acoustic transducer, disposed within the implantable medical device; and a second acoustic transducer, disposed on a lead or catheter coupled with the implantable medical device.

44. The system of claim 41, wherein the implantable medical device includes a controller that initiates or modifies a therapy using the detected change in the physiological condition obtained from the responsive acoustic energy.

45. The system of claim 41, wherein the implantable medical device includes a controller that is adapted to determine whether ischemia is present in response to a change in physical property obtained from the responsive acoustic energy.

46. The system of claim 45, comprising:

multiple pacing electrodes disposed at different locations within a subject, the electrodes communicatively coupled with the controller; and wherein the controller is adapted to modify the selected electrodes or timing of pacing pulses delivered by the electrodes in response to a determination of ischemia.

* * * * *